United States Patent
Tufts et al.

(10) Patent No.: US 10,194,701 B1
(45) Date of Patent: Feb. 5, 2019

(54) POST-OPERATIVE SHOWER BRASSIERE

(71) Applicants: Wendi Tufts, Mesa, AZ (US); Robert Tufts, Mesa, AZ (US)

(72) Inventors: Wendi Tufts, Mesa, AZ (US); Robert Tufts, Mesa, AZ (US)

( * ) Notice: Subject to any disclaimer, the term of this patent is extended or adjusted under 35 U.S.C. 154(b) by 44 days.

(21) Appl. No.: 15/602,262

(22) Filed: May 23, 2017

(51) Int. Cl.
*A41C 3/00* (2006.01)
*A41C 3/12* (2006.01)
*A61M 1/00* (2006.01)
*A61M 27/00* (2006.01)

(52) U.S. Cl.
CPC .......... *A41C 3/0064* (2013.01); *A41C 3/0035* (2013.01); *A41C 3/12* (2013.01); *A61M 1/0021* (2013.01); *A61M 27/00* (2013.01); *A41B 2400/52* (2013.01); *A61M 2209/088* (2013.01); *A61M 2210/1007* (2013.01)

(58) Field of Classification Search
CPC ......... A41C 3/00; A41C 3/0014; A41C 3/144; A41C 3/06; A41C 3/0057; A41C 3/12; A41C 3/126; A41C 3/065
USPC ...................................... 450/81, 41, 39, 106
See application file for complete search history.

(56) References Cited

U.S. PATENT DOCUMENTS

| | | | | |
|---|---|---|---|---|
| 2,289,679 A | * | 7/1942 | Porter | A41C 3/144 450/57 |
| 2,524,620 A | * | 10/1950 | Esther | A41C 3/06 450/41 |
| 2,988,087 A | * | 6/1961 | Krieger | A41C 3/06 450/81 |
| 3,254,653 A | * | 6/1966 | Krieger | A41C 3/00 450/39 |
| 6,036,577 A | * | 3/2000 | Coburn | A41C 3/065 450/57 |
| 6,338,665 B1 | * | 1/2002 | Dawson | A41C 3/065 450/37 |
| 6,390,885 B1 | | 5/2002 | Brooks | |
| 6,446,268 B1 | * | 9/2002 | Lazarian | A41B 11/126 2/237 |
| 7,228,809 B2 | * | 6/2007 | Angelino | A41D 27/245 112/440 |
| D550,368 S | | 9/2007 | Hankins | |

(Continued)

FOREIGN PATENT DOCUMENTS

WO 2015195170 12/2015

OTHER PUBLICATIONS

U.S. Appl. No. 62/267,998, filed May 8, 2001, LeBlanc.

*Primary Examiner* — Gloria Hale
(74) *Attorney, Agent, or Firm* — Kyle A. Fletcher, Esq.

(57) ABSTRACT

The post-operative shower brassiere is adapted for use with a patient. The post-operative shower brassiere is a garment. The post-operative shower brassiere is intended to be a single use disposable garment. The post-operative shower brassiere is intended for use during bathing or showering. The post-operative shower brassiere is formed from a water impermeable material. The post-operative shower brassiere forms a water impermeable seal around one or more breasts of the patient to protect post-surgical wounds received from breast surgery. Specifically, the post-operative shower brassiere protects the one or more breasts from the water used in bathing activities. The post-operative shower brassiere comprises a garment and a sealing strip. The sealing strip is applied to the interior surface of the garment.

16 Claims, 3 Drawing Sheets

(56) References Cited

U.S. PATENT DOCUMENTS

| | | | |
|---|---|---|---|
| 7,422,508 B2* | 9/2008 | Bentham | A41C 3/0014 |
| | | | 2/243.1 |
| 7,645,916 B2* | 1/2010 | Rasor | A61L 15/60 |
| | | | 442/123 |
| 7,775,851 B2 | 8/2010 | Sgro | |
| D658,352 S | 5/2012 | Pinner | |
| 8,684,789 B2* | 4/2014 | Gramelspacher | A41C 3/065 |
| | | | 450/81 |
| 9,277,773 B2 | 3/2016 | Blackwell | |
| 9,516,905 B2* | 12/2016 | Pagnon | A41C 3/10 |
| 2003/0040256 A1* | 2/2003 | Waitz | A41C 3/12 |
| | | | 450/86 |
| 2003/0186620 A1* | 10/2003 | Kaye | A41F 15/005 |
| | | | 450/86 |
| 2005/0020184 A1* | 1/2005 | Izcoa | A41C 3/12 |
| | | | 450/86 |
| 2005/0266770 A1* | 12/2005 | Henricksen | A41C 3/0007 |
| | | | 450/1 |
| 2006/0223415 A1* | 10/2006 | Watrin | A41C 3/0014 |
| | | | 450/39 |
| 2011/0143633 A1* | 6/2011 | Zhang | A41C 3/14 |
| | | | 450/39 |
| 2012/0225607 A1* | 9/2012 | Martinet | A41C 3/126 |
| | | | 450/41 |
| 2013/0115852 A1 | 5/2013 | Blackwell | |
| 2014/0154949 A1* | 6/2014 | Pagnon | A41C 3/00 |
| | | | 450/57 |
| 2014/0312091 A1 | 10/2014 | Anderson | |
| 2015/0080860 A1 | 3/2015 | Farrell | |

* cited by examiner

POST-OPERATIVE SHOWER BRASSIERE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of personal and domestic articles including wearing apparel, more specifically, a brassiere specially adapted for medical use.

SUMMARY OF INVENTION

The post-operative shower brassiere is adapted for use with a patient. The post-operative shower brassiere is a garment. The post-operative shower brassiere is intended to be a single use disposable garment. The post-operative shower brassiere is intended for use during bathing or showering. The post-operative shower brassiere is formed from a water impermeable material. The post-operative shower brassiere forms a water impermeable seal around one or more breasts of the patient to protect post-surgical wounds received from breast surgery. Specifically, the post-operative shower brassiere protects the one or more breasts from the water used in bathing activities. The post-operative shower brassiere comprises a garment and a sealing strip. The sealing strip is applied to the interior surface of the garment.

These together with additional objects, features and advantages of the post-operative shower brassiere will be readily apparent to those of ordinary skill in the art upon reading the following detailed description of the presently preferred, but nonetheless illustrative, embodiments when taken in conjunction with the accompanying drawings.

In this respect, before explaining the current embodiments of the post-operative shower brassiere in detail, it is to be understood that the post-operative shower brassiere is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the post-operative shower brassiere.

It is therefore important that the claims be regarded as including such equivalent construction insofar as they do not depart from the spirit and scope of the post-operative shower brassiere. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
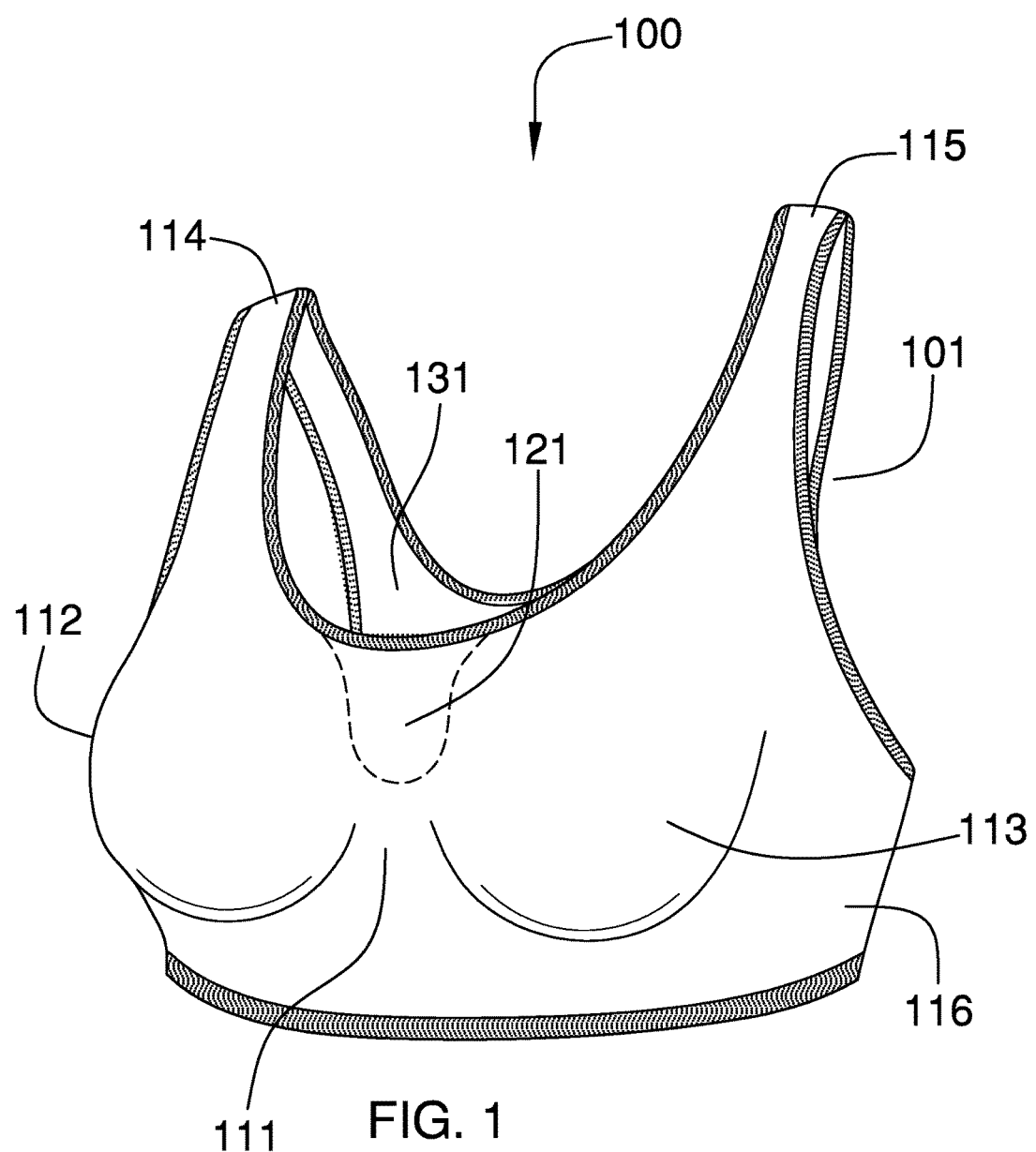
FIG. 1 is a perspective view of an embodiment of the disclosure.
Figure 2:
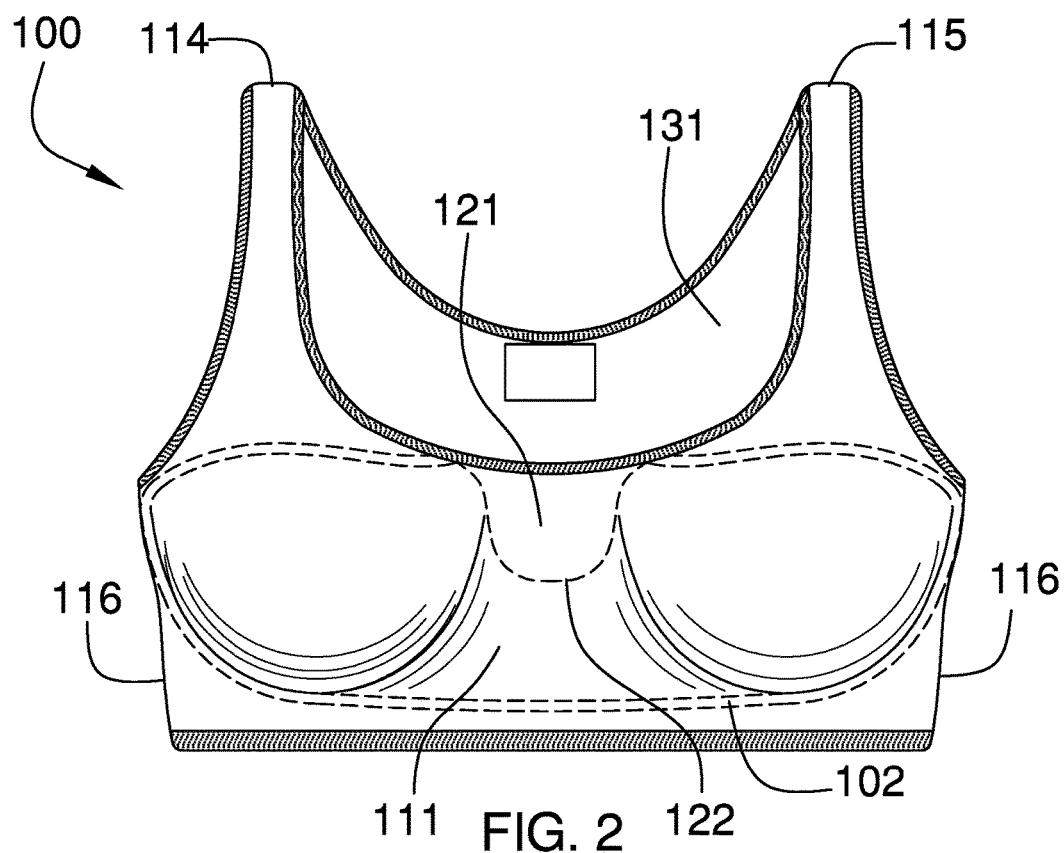
FIG. 2 is a front view of an embodiment of the disclosure.
Figure 3:
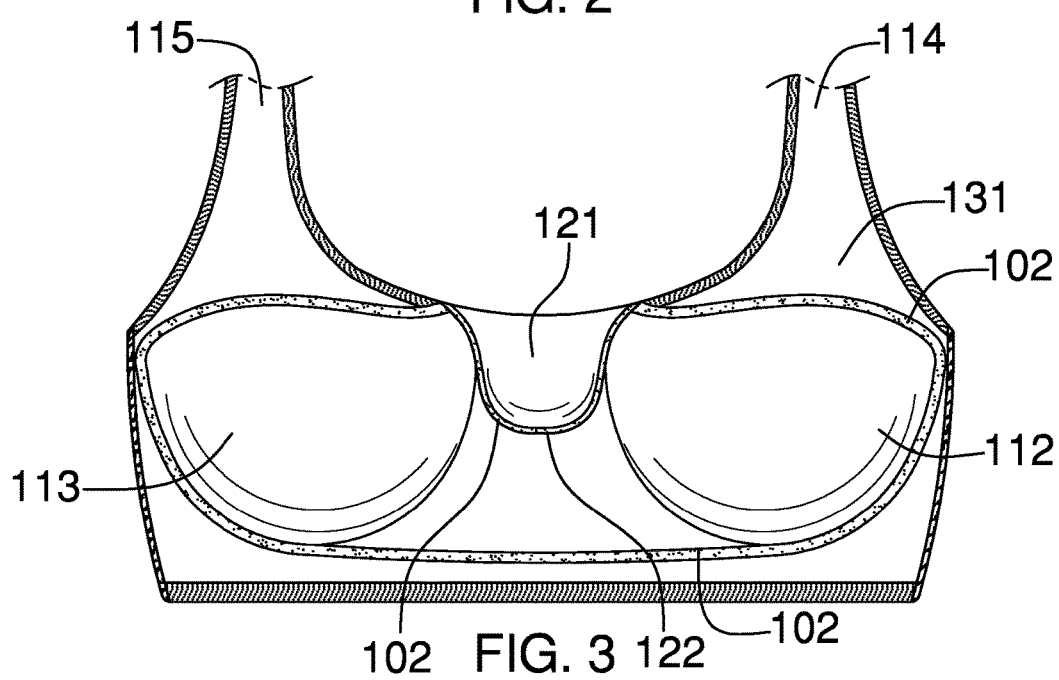
FIG. 3 is a cross-sectional rear view of an embodiment of the disclosure.
Figure 4:
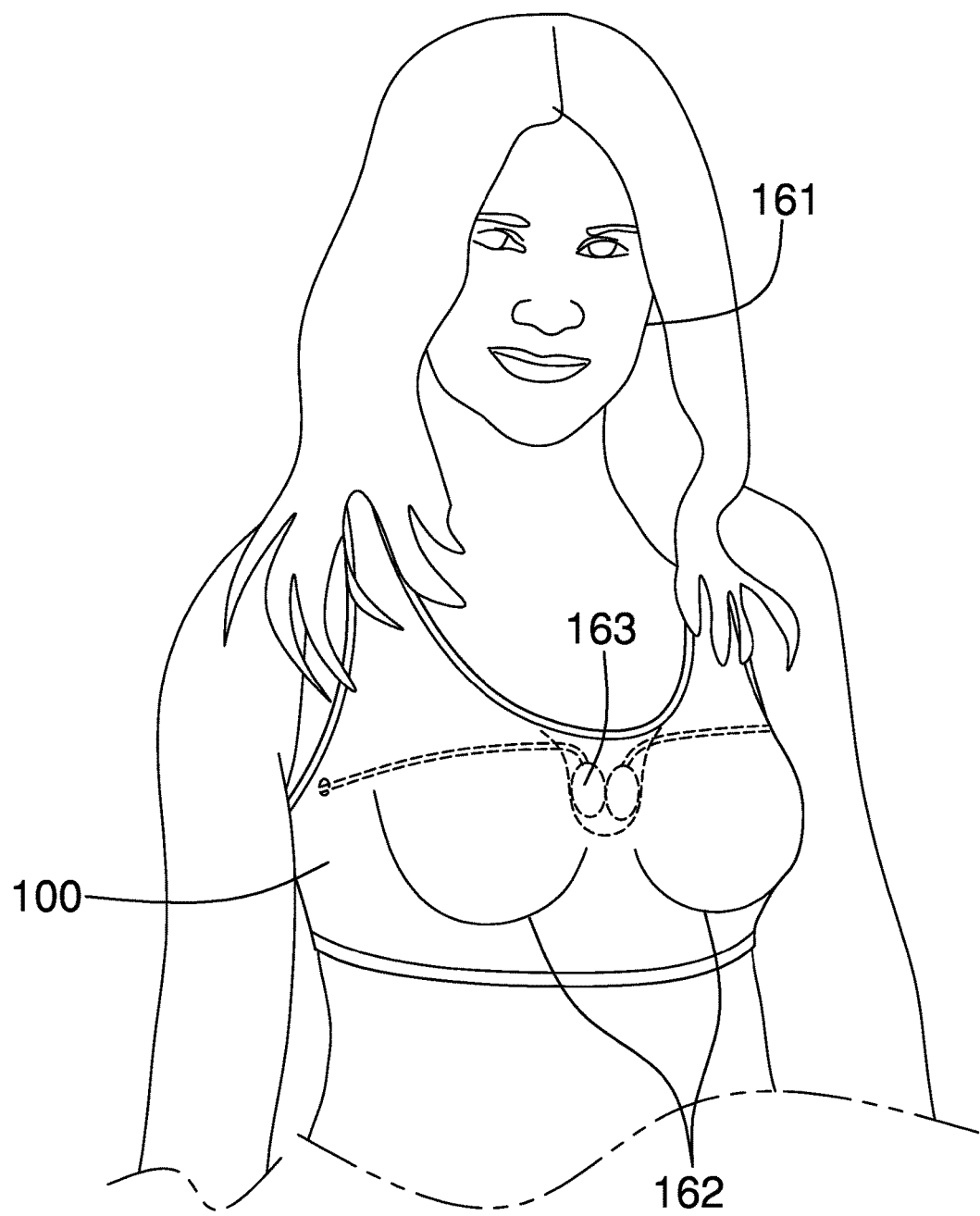
FIG. 4 is an in use view of an embodiment of the disclosure.

Detailed reference will now be made to one or more potential embodiments of the disclosure, which are illustrated in FIGS. 1 through 4.

The post-operative shower brassiere 100 (hereinafter invention) is adapted for use with a patient 161. The invention 100 is a garment 101. The invention 100 is intended to be a single use disposable garment 101. The invention 100 is intended for use during bathing or showering. The invention 100 is formed from a water impermeable material. The invention 100 forms a water impermeable seal around one or more breasts 162 of the patient 161 to protect post-surgical wounds received from breast surgery. Specifically the invention 100 protects the one or more breasts 162 from the water used in bathing activities. The invention 100 comprises a garment 101 and a sealing strip 102. The sealing strip 102 is applied to the interior surface 131 of the garment 101. The patient 161 refers to a woman who is wearing the garment 101. The patient 161 is further defined with one or more breasts 162 who uses one or more drain bulbs 163. Each of the one or more drain bulbs 163 is a fluid collection device that drains bodily fluids away from the surgical wound as part of the healing process.

The purpose of the garment 101 is to protect one or more breasts 162 of the patient 161. Specifically, the garment 101 prevents bathing water from interfering with the healing of post-surgical wounds received from breast surgery. The garment 101 is sized such that: 1) force must be applied to elongate the garment 101 as the garment 101 is being put on by the patient 161; and, 2) the garment 101 will not return to its relaxed shape while the garment 101 is being worn by the patient 161. The force of the garment 101 pressing against the skin of the patient 161 forms a seal that prevents water from reaching the surgical wound of the patient 161.

The garment 101 is a water impermeable garment 101. The garment 101 is disposable. The garment 101 is formed from a sheeting. The sheeting is formed from a water impermeable elastomeric material. The garment 101 is worn via the patient 161 as a brassiere. The garment 101 is a disposable garment 101 intended for a single medical use.

The garment 101 comprises a center panel 111, a right cup 112, a left cup 113, a right strap 114, a left strap 115 and a brassiere band 116.

The center panel 111 refers to the segment of the garment that is between the right cup 112 and the left cup 113. The right cup 112 refers to a smooth molded concave surface (as seen from the interior surface 131) that forms a cavity within the garment 101. The right cup 112 is the structure that supports the right breast from the one or more breasts 162 of the patient 161. The left cup 113 refers to a smooth molded concave surface (as seen from the interior surface 131) that forms a cavity within the garment 101. The left cup 113 is the structure that supports the left breast from the one or more breasts 162 of the patient 161. Methods to form cups into a sheeting is well known and documented in the textile and apparel arts.

The right strap 114 is a load bearing strap structure that distributes the load managed by the garment 101 to the right shoulder of the patient 161. The left strap 115 is a load bearing strap structure that distributes the load managed by the garment 101 to the left shoulder of the patient 161. The brassiere band 116 is an elastic band that attaches the garment 101 around the sides and the back of the patient 161. Methods to form and use one or more shoulder straps is well known and documented in the textile and apparel arts.

The sealing strip 102 is a protective bead that is formed on the interior surface 131 of the garment 101 for the purpose of creating a water impermeable seal around the one or more breasts 162. The interior surface 131 refers to the surface of the garment 101 that is proximal to the skin of the patient 161. The sealing strip 102 is formed from an elastomeric silicone based adhesive. The silicone based adhesive used to form the sealing strip 102 is a pressure sensitive adhesive. When the elastic force from the garment 101 is applied to the sealing strip 102, the elastic nature of the silicone based adhesive forces the sealing strip 102 to expand into surface irregularities that may exist within the skin of the patient 161 and the interior surface 131 of the garment 101 thereby forming the primary protective water impermeable barrier of the invention 100.

The pressure of the elastic force of the garment 101 against the skin of the patient 161 further inhibits the flow of bathing water to the sealing strip 102 thereby forming a secondary protective water impermeable barrier in support of the sealing strip 102.

The sealing strip 102 is applied to the interior surface 131 of the garment 101 as a loop. The loop of the sealing strip 102 encloses the right cup 112 and the left cup 113 of the garment 101 such that the sealing strip 102 encloses the one or more breasts 162 of the patient 161 when the invention 100 is worn as intended.

The loop formed by the sealing strip 102 has further formed in it a drain bulb notch 122. The drain bulb notch 122 is formed from the superior edge of the loop of the sealing strip 102. As seen from within the area enclosed by the loop of the sealing strip 102 the drain bulb notch 122 forms a convex curvature within the loop of the sealing strip 102 that is used to form the drain bulb pocket 121. The drain bulb pocket 121 is discussed in greater detail in the next two paragraphs.

The drain bulb pocket 121 is a storage space that forms the superior region of the center panel 111. The drain bulb pocket 121 is accessed from the superior edge of the center panel 111. The storage space is formed in the space between the drain bulb pocket 121 and the drain bulb notch 122. Specifically, the drain bulb notch 122 allows the portion of the center panel 111 that is superior to the drain bulb notch 122 to be pulled away from the skin of the patient 161 without the risk of bathing water entering either the right cup 112 or the left cup 113.

The one or more drain bulbs 163 can be placed into the drain bulb pocket 121: 1) by pulling the garment 101 away from the skin of the patient 161; 2) placing the one or more drain bulbs 163 into the drain bulb pocket 121; and, 3) releasing the garment 101. The pressure of the elastic force of the garment 101 applied against the one or more drain bulbs 163 will securely hold the one or more drain bulbs 163 in position against the patient 161.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Band: As used in this disclosure, a band is a flat loop of material.

Cavity: As used in this disclosure, a cavity is an empty space or negative space that is formed within an object.

Concave: As used in this disclosure, concave is used to describe: 1) a surface that resembles the interior surface of a sphere; or, 2) a function with a curvature structure wherein a chord that connects any two points of the function will be lesser than (graphically below) or equal to the value of the function at any point along the chord.

Convex: As used in this disclosure, convex is used to describe: 1) a surface that resembles the outer surface of a sphere; or, 2) a function with a curvature structure wherein a chord that connects any two points of the function will be greater than (graphically above) or equal to the value of the function at any point along the chord.

Disposable: As used in this disclosure, disposable is an adjective that refers to an object that is designed and intended for a single use. Within this context, an object would be considered disposable if it is not reusable after its initial use.

Elastic: As used in this disclosure, an elastic is a material or object that deforms when a force is applied to it and that is able to return to its original shape after the force is removed. A material that exhibits these qualities is also referred to as an elastomeric material.

Elastic Band: As used in this disclosure, an elastic band is a loop of textile that is formed using elastic material that can stretched. Alternatively, the elastic band can be a sheeting that is formed from latex, spandex, or an elastic plastic film that can be stretched.

Exterior: As used in this disclosure, the exterior is use as a relational term that implies that an object is not contained within the boundary of a structure or a space.

Inferior: As used in this disclosure, the term inferior refers to a directional reference that is parallel to and in the same direction as the force of gravity.

Interior: As used in this disclosure, the interior is use as a relational term that implies that an object is contained within the boundary of a structure or a space.

Loop: As used in this disclosure, a loop is the length of a first linear structure that is joined at the ends forming an enclosed area.

Patient: As used in this disclosure, a patient is a person who is designated to receive a medical treatment, therapy or service. The term patient may be extended to an animal when used within the context of the animal receiving veterinary treatment or services Pocket: As used in this disclosure, a pocket is a small pouch or storage space that is formed into a garment. Pockets are often formed by joining a second textile or a second sheeting to a first textile or a first sheeting, respectively, by sewing or heat sealing respectively.

Pressure Sensitive Adhesives: As used in this disclosure, a pressure sensitive adhesive is an adhesive that is a permanently tacky adhesive that is activated by the application of pressure.

Relaxed Shape: As used in this disclosure, a structure is considered to be in its relaxed state when no shear, strain, or torsional forces are being applied to the structure.

Removable Adhesive: As used in this disclosure, a removable adhesive is an commercially available adhesive that is designed with a lower tack, or stickiness, such that a first object is attached to a second object with a removable adhesive the first object can be readily removed in a manner that ideally, though not necessarily practically, leaves behind no adhesive residue on the second object. A repositionable adhesive is a subset of removable adhesives that are intended to allow the first object to be reattached to a third object or the second object in the initial or a different position. Within this disclosure, a removable adhesive is assumed to include repositionable adhesives.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sheeting: As used in this disclosure, sheeting is a material, such as a textile, a plastic, or a metal foil, in the form of a thin flexible layer or layers.

Silicone: As used in this disclosure, silicone is a substance formed from silicon (Si) and oxygen (O) that forms the backbone of polymer type chains similar to polymers that are formed by carbon.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Superior: As used in this disclosure, the term superior refers to a directional reference that is parallel to and in the opposite direction of the force of gravity.

Tape: As used in this disclosure, tape refers to a flexible and narrow strip of textile or sheeting that fastens, secures, or strengthens an object.

Underclothing: As used in this disclosure, underclothing refers to garments that are intended to be worn next to the skin. Underclothing is often worn in conjunction with an outer layer of clothing.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A garment adapted for medical use comprising
a garment and a sealing strip;
wherein the garment is further defined with an interior surface;
wherein the sealing strip is applied to the interior surface of the garment;
wherein the garment is adapted for use by a patient;
wherein the garment is formed from a water impermeable material;
wherein the garment is adapted to form a water impermeable seal around one or more breasts of the patient;
wherein the garment is disposable;
wherein the garment is sized such that the garment will not return to its relaxed shape while the garment is being worn by the patient;
wherein the force of the garment pressing against the skin of the patient forms a water impermeable seal;
wherein the garment is formed from a sheeting;
wherein the sheeting is formed from a water impermeable elastomeric material;
wherein the garment comprises a center panel, a right cup, a left cup, a right strap, a left strap and a brassiere band;
wherein the center panel, the right cup, the left cup, the right strap, the left strap and the brassiere band are formed within the sheeting.

2. The garment adapted for medical use according to claim 1
wherein the center panel attaches the left cup to the right cup;
wherein the right cup is a molded concave surface that forms a cavity within the garment;
wherein the right cup is the structure that is adapted to support a right breast of the patient;
wherein the left cup is a molded concave surface that forms a cavity within the garment;
wherein the left cup is the structure that is adapted to support a left breast of the patient;
wherein the right strap is a load bearing strap structure that is adapted to distribute the load managed by the garment to the right shoulder of the patient;
wherein the left strap is a load bearing strap structure that is adapted to distribute the load managed by the garment to the left shoulder of the patient;
wherein the brassiere band is an elastic band that is adapted to attach the garment around the sides and the back of the patient.

3. The garment adapted for medical use according to claim 2
wherein the sealing strip is formed by running a protective bead in a line on one interior surface of the garment that lies adjacent to a skin surface of the patient.

4. The garment adapted for medical use according to claim 3
wherein the sealing strip is formed from an elastomeric, pressure sensitive, silicone based adhesive;

wherein an elastic nature of the silicone based adhesive cause the sealing strip to expand into surface irregularities within a skin of the patient; and wherein the elastic nature of the silicone based adhesive causes the sealing strip to expand into surface irregularities within the interior surface of the garment.

5. The garment adapted for medical use according to claim 4 wherein the sealing strip is applied to the interior surface of the garment as a loop;

wherein the loop of the sealing strip encloses the right cup and the left cup of the garment such that the sealing strip encloses at least one breast or both breasts of the patient.

6. The garment adapted for medical use according to claim 5 wherein the loop formed by the sealing strip further comprises a drain bulb notch;

wherein the drain bulb notch is formed from a superior edge in the loop of the sealing strip;

wherein the drain bulb notch forms a convex curvature within the loop of the sealing strip.

7. The garment adapted for medical use according to claim 6 wherein a drain bulb pocket is a storage space formed in a superior region of the center panel;

wherein the drain bulb pocket is accessed from a superior edge of the center panel;

wherein the storage space is formed in a space between the drain bulb pocket and the drain bulb notch;

wherein the drain bulb notch allows a portion of the center panel that is superior to the drain bulb notch to be pulled away from the skin surface of the patient;

wherein the one or more drain bulbs are placed into the drain bulb pocket;

wherein the garment secures the one or more drain bulbs in position against the patient.

8. The garment adapted for medical use according to claim 1 wherein the sealing strip is formed by running a protective bead in a line on one interior surface of the garment that lies adjacent to a skin surface of the patient.

9. The garment adapted for medical use according to claim 8 wherein the sealing strip is formed from an elastomeric, pressure sensitive, silicone based adhesive;

wherein an elastic nature of the silicone based adhesive cause the sealing strip to expand into surface irregularities within a skin of the patient; and wherein the elastic nature of the silicone based adhesive causes the sealing strip to expand into surface irregularities within the interior surface of the garment.

10. The garment adapted for medical use according to claim 9 wherein the sealing strip is applied to the interior surface of the garment as a loop.

11. The garment adapted for medical use according to claim 10 wherein the loop formed by the sealing strip further comprises a drain bulb notch;

wherein the drain bulb notch is formed from a superior edge in the loop of the sealing strip;

wherein the drain bulb notch forms a convex curvature within the loop of the sealing strip.

12. The garment adapted for medical use according to claim 11 wherein a drain bulb pocket is a storage space formed in a superior region of the center panel;

wherein the drain bulb pocket is accessed from a superior edge of the center panel;

wherein the storage space is formed in a space between the drain bulb pocket and the drain bulb notch;

wherein the drain bulb notch allows a portion of the center panel that is superior to the drain bulb notch to be pulled away from the skin surface of the patient;

wherein the one or more drain bulbs are placed into the drain bulb pocket;

wherein the garment secures the one or more drain bulbs in position against the patient.

13. The garment adapted for medical use according to claim 12 wherein the garment is a water impermeable garment;

wherein the garment is disposable;

wherein the garment is sized such that force must be applied to elongate the garment as the garment is being put on by the patient;

wherein the garment is sized such that the garment will not return to its relaxed shape while the garment is being worn by the patient;

wherein the force of the garment pressing against the skin of the patient forms a water impermeable seal.

14. The garment adapted for medical use according to claim 13 wherein the garment is formed from a sheeting;

wherein the sheeting is formed from a water impermeable elastomeric material.

15. The garment adapted for medical use according to claim 14 wherein the garment comprises a center panel, a right cup, a left cup, a right strap, a left strap and a brassiere band;

wherein the center panel, the right cup, the left cup, the right strap, the left strap and the brassiere band are formed within the sheeting.

16. The garment adapted for medical use according to claim 15 wherein the center panel attaches the left cup to the right cup;

wherein the right cup is a molded concave surface that forms a cavity within the garment;

wherein the right cup is the structure that supports a right breast selected from the one or more breasts of the patient;

wherein the left cup is a molded concave surface that forms a cavity within the garment;

wherein the left cup is the structure that supports a left breast selected from the one or more breasts of the patient;

wherein the right strap is a load bearing strap structure that distributes the load managed by the garment to the right shoulder of the patient;

wherein the left strap is a load bearing strap structure that distributes the load managed by the garment to the left shoulder of the patient;

wherein the brassiere band is an elastic band that attaches the garment around the sides and the back.

* * * * *